United States Patent [19]

Perel

[11] Patent Number: 5,769,082
[45] Date of Patent: Jun. 23, 1998

[54] METHOD OF ASSESSING CARDIOVASCULAR FUNCTION

[76] Inventor: Azriel Perel, Moshav Bar Giyora, D.N. Ha'ela, Israel, 99880

[21] Appl. No.: 503,907

[22] Filed: Jul. 18, 1995

[51] Int. Cl.[6] ........................................................ A61B 5/02
[52] U.S. Cl. ................................................................ 128/671
[58] Field of Search ........................... 128/668, 670–672, 128/695, 697, 713, 716, 719, 747

[56] References Cited

U.S. PATENT DOCUMENTS

| | | |
|---|---|---|
| 3,381,590 | 5/1968 | Boyle et al. . |
| 4,592,364 | 6/1986 | Pinto .................................... 128/695 X |
| 5,103,814 | 4/1992 | Maher . |
| 5,188,098 | 2/1993 | Hoffman et al. . |
| 5,241,966 | 9/1993 | Finkelstein et al. ..................... 128/713 |
| 5,584,298 | 12/1996 | Kabal ..................................... 128/672 |
| 5,615,684 | 4/1997 | Hagel et al. ............................. 128/670 |

FOREIGN PATENT DOCUMENTS

WO 87/06040  10/1987  WIPO .

OTHER PUBLICATIONS

P. Coriat et al, "A comparison of Systolic Blood Pressure Variations and Echocardiographic Estimates of End–Diastolic Left Ventricular Size in Patients After Aortic Surgery", Anesthesia & Analgesia, vol. 78, No. 1, Jan. 1994, pp. 46–53.

R. Pizov et al. "The Arterial Pressure Waveform During Acute Ventricular Failure and Synchronized External Chest Compression", Anesthesia and Analgesia, vol. 68, No. 2, Feb. 1989, pp. 150–156.

*Primary Examiner*—Jennifer Bahr
*Assistant Examiner*—Samuel Gilbert
*Attorney, Agent, or Firm*—Sixbey, Friedman, Leedom & Ferguson; David S. Safran

[57] ABSTRACT

Disclosed is a method of analyzing changes in continuously measured hemodynamic parameters in response to a set of predetermined changes in airway pressure or tidal volume. The method is generally called "respiratory systolic variation test" (RSVT). The analysis of the change in the hemodynamic parameter in response to such airway pressure maneuver serves as a non-invasive or minimally invasive method of assessing the cardiovascular status, particularly the volume responsiveness of the patient.

13 Claims, 11 Drawing Sheets

METHOD OF ASSESSING CARDIOVASCULAR FUNCTION

The invention relates to a method by which the cardiovascular status of patients who are mechanically ventilated can be assessed by analyzing changes in hemodynamic parameters in response to predetermined changes in ventilation.

Cardiovascular function has to be frequently monitored in patients that are mechanically ventilated, either during anesthesia and surgery or due to some disease state. The aim of such monitoring is mainly to assess the adequacy of the blood volume status of the patient and to assess cardiac function. Cardiovascular function is being widely assessed by simply measuring the blood pressure and heart rate. However, these parameters alone are notorious for being too insensitive and too unspecific to assess and follow cardiovascular changes in sick patients.

There are some more advanced methods available of measuring cardiovascular function in patients who are mechanically ventilated. One of these methods is the measurement of the central venous pressure (CVP) by a catheter that is introduced through a vein into the right atrium or its vicinity (Kaye, W. E., Dubin, H. G.: Vascular Cannulation. in, Civetta JM et al, eds, Critical Care, JB. Lippincott, 1988, pp 214–219). The pressure in the right atrium (CVP) however, does not always reflect the pressure in the left side of the heart, i.e., the filling pressure of the left ventricle, which is the major blood pumping mechanism. Furthermore, the CVP may be elevated due to independent failure of the right heart or some lung disease, while the left atrial pressure is, in effect, low. Finally, estimating the filling volume of a heart chamber by measuring pressure is hindered by the compliance of that chamber.

A further method which is often used in critically ill patients or those who undergo major surgery is the introduction of a baloon—tipped pulmonary artery (Swan-Ganz) catheter. Thereby the pulmonary capillary wedge pressure (PCWP), which is an estimate of the left atrial pressure (Clark, C. A., Harman, E. M.: Hemodynamic monitoring: Pulmonary Artery Catheters in, Civetta JM et al, eds., Critical Care, JB Lippincott, 1988, pp 293–6) hereafter referred to as (Clark), is measured. However, like the CVP, the PCWP is influenced by the compliance of the left ventricle. Furthermore, since the pulmonary circulation is situated between the tip of the catheter and the left atrium, high airway pressures during mechanical ventilatory support may cause a false elevation of the PCWP.

These problems and also the well-known pitfalls in the interpretation of filling pressures led to the practice that in patients who suffer from circulatory failure and in whom it is crucial to diagnose the pathological mechanism of such failure for further therapy, a graded fluid loading must be performed (Majid P. A., Roberts, R.: Heart Failure in, Civetta JM et al, eds., Critical Care, JB Lippincott, 1988, pp 948–952). Such a procedure is very time-consuming and is not done very frequently.

It is also known that in addition to the pitfalls interpreting CVP and PCWP values, the insertion of CVP and especially of pulmonary artery catheters is costly, involves considerable training and associated with a multitude of reported complications (Clark).

Another new technique for cardiovascular assessment is the so-called transesophageal echocardiography, which is an imaging technique that is mainly used for evaluating the size of the heart chambers and the status of myocardial contractility (Konstadt, S. et al: Transesophageal Echocardiography in, Kaplan JA, ed, Cardiac Anesthesia, Saunders, 1993, p. 364). However, this method is also very costly, requires a lot of training, can be used for only one patient at a time, cannot be used continuously for longer periods of time, and is difficult to interpret in real time.

Furthermore, a method called pressure waveform analysis has been recently presented. According to this method, the changes in the systolic blood pressure during one mechanical breath cycle are clinically measured and used for cardiovascular assessment, Normally, the arterial pressure responds in a bi-phasic manner to a mechanical breath. An early increase in the systolic pressure (delta up, dUp) is caused due to transiently increased stroke volumes. The delta up is then followed by a decrease in the systolic pressure (delta down, dDown), which occurs due to the decrease in the amount of blood entering the right heart (venous return), due in turn to the increase in intrathoracid pressure during the mechanical breath. The difference between the maximal and minimal values of the systolic pressure during one mechanical breath is termed "systolic pressure variation" (SPV). It is known that the SPV and dDown are very sensitive indicators of the filling status and that they reflect this status better than PCWP and CVP (Perel, A., Pizov, R., Cotev, S.: The Systolic Pressure Variation Is A Sensitive Indicator Of Hypovolemia In Ventilated Dogs Subjected To Graded Hemorrhage, Anesthesiology 67; 498–502, 1987; Pizov, R., Ya'ari, Y., Perel, A.: Systolic Pressure Variation Is Greater During Hemorrhage Than During Sodium Nitroprusside Induced Hypotension In Ventilated Dogs, Anesth. Analg. 67; 170–174, 1988 and Pizov, R., Ya'ari, Y., Perel, A.: The Arterial Pressure Waveform During Acute Ventricular Failure And Synchronized External Chest Compression, Anesth. Analg. 68; 150–156, 1989) hereafter referred to as (Perel). Pressure waveform analysis, however, has not been used commercially up to now.

It is an object of the present invention to provide a new method for assessing cardiovascular function in ventilated patients which does not have the disadvantages of the methods used in the prior art as discussed above.

The new method is to assess the responsiveness of the patient to the administration of intravenous fluids obviate the need for actual volume loading and the performance of invasive measurements that are currently used for such assessments.

This object is achieved by the method and the apparatus as defined in the claims.

The respiratory maneuver of the invention is composed of a predetermined sequence of a few, preferably between 2 and 10, more preferably 2, 3, or 4, consecutive tidal volumes of varying magnitude, which will affect the filling of the heart in a graded manner. In general, these incremental changes in the airway pressure are used as a challenge to the cardiovascular system. The increase in airway pressure that is associated with mechanical ventilation causes a series of changes in the filling and performance of the heart chambers.

The most important hemodynamic effects of such respiratory maneuver include normally:

(a) a decrease in the venous return with relative emptying of the right atrium and ventricle, leading eventually to a transient reduction in left ventricular stroke outputs and a transient decrease in the systolic blood pressure;

(b) an early increase in the filling of the left atrium and ventricle due to the squeezing of blood from the pulmonary vasculature. This increased preload causes an early transient increase in left ventricular stroke output during the mechanical breath;

(c) a decrease in left ventricular afterload which may also augment left ventricular stroke output especially during congestive heart failure. The main mechanism of this phenomenon is the partial transmission of the increased airway pressure to the left ventricle and thoracid aorta relative to the subdiaphragmatic aorta.

Thus the normal response of the left ventricular stroke output to a mechanical breath is bi-phasic and includes an early increase followed by a later decrease.

More specifically, since the major cardiovascular effect of a mechanical breath is the reduction in venous return, a series of gradually increasing tidal volumes will cause a gradual decrease in venous return. The effects of this graded decrease in venous return on the cardiac output will be normally reflected by graded decreases in left ventricular stroke output and any physiological parameter that is influenced by it, e.g., arterial pressure, plethysmographic signal, Doppler signal, etc.

In addition, however, the respiratory maneuver may also induce respective increases in the hemodynamic variable (dUp), signifying the positive cardiovascular effect of increased airway pressure, which characterizes fluid overload with or without heart failure (Perel and Coriat, P., Vrillon, M., Perel, A. et al: A Comparison Of Systolic Blood Pressure Variations And Echocardiographic Estimates Of End-Diastolic Left Ventricular Size In Patients After Aortic Surgery, Anesth. Analg. 78; 46–53, 1994).

According to the invention, it is possible to measure the changes in the above parameters in response to the sequential respiratory maneuver. Such changes will be expressed by either absolute units, or preferably by percent changes of cardiovascular parameter per unit change in airway pressure or tidal volume (preset or measured).

The method of the present invention is also called "respiratory systolic variation test" (RSVT).

It is also preferred that short apnea is induced prior to carrying out the respiratory maneuver described above.

The invention also provides an apparatus for carrying out the above-described respiratory maneuver, namely in providing a few consecutive tidal volumes of varying magnitude, preferably after short apnea, and monitoring the response of a hemodynamic variable to these tidal volumes of varying magnitude. The apparatus of the invention consists essentially of a respirator which is preferably linked to a monitor, said respirator and said monitor being preferably equipped with a specially designed software. The ventilator delivers, on demand or automatically, a series of tidal volumes of varying magnitude at a preset configuration and rate, preferably after short apnea. The size of these tidal volumes is not critical to the present invention and may be absolutely preset, set according to the patient's weight (e.g., 5, 10, 15 and 20 ml/kJ), or pressure preset, i.e., the ventilator will be programmed to deliver tidal volumes according to varying degrees of preset pressures, preferably using a pressure controlled ventilation mode. Either the preset or the actually measured volumes or pressures may be used in the calculations.

The time difference between two tidal volumes and hence the time period for the total sequence is not critical either and can either be preset or chosen by those skilled in the art as required by the actual situation. For example, the time difference between two tidal volumes is in the range of 4 to 10 seconds and hence the total time period for the sequence of, e.g., four consecutive tidal volumes of varying magnitude is, e.g., in the range of 16 to 40 seconds.

The monitor will preferably be equipped with special software that will measure the changes in the hemodynamic parameter (e.g., blood pressure, plethysmographic signal, Doppler echo, etc.) during and following the variations of the airway pressure. The minimal systolic value of the signal of the chosen hemodynamic parameter will be recorded after each step of the airway maneuver, and a line of best fit can be plotted. The slope of that curve, which is the difference in the hemodynamic signal over the difference in airway pressure or volume, will be calculated and expressed according to the units of the measured parameter, e.g., mmHg of blood pressure/ml of tidal volume, mmHg blood pressure/ $cmH_2O$ of airway pressure, % change in systolic pressure/ $cmH_2O$ of airway pressure, t change in plethysmographic amplitude/ml of tidal volume, etc. The actual expired tidal volume or airway pressure can be preferably measured and plotted on the graph. Alternatively, the preset delivered tidal volumes or pressures can be used for plotting.

In addition to the minimal values mentioned above, the maximal values of the measured hemodynamic signal, e.g., maximal systolic blood pressure, after each breath will be preferably measured following each change in airway pressure. A curve depicting the slope of the change in that parameter relative to the change in tidal volume and/or airway pressure will be preferably plotted. The slope of this graph is a possible parameter assessing the degree by which an increase in airway pressure augments cardiac output.

Thus the two lines of best fit, that connecting the lowest values and that connecting the highest values, that are induced by the respiratory maneuver of the invention, create two angles relative to a reference horizontal line. The ratio of these angles to each other provides an additional parameter that reflects the status of intravascular filling and cardiac performance.

The airway pressure maneuver, i.e., the deliverance of a few incremental volumes/pressures can be preferably incorporated into existing ventilators using either microprocessors or electronic technology or can be delivered by a stand-alone device. The main software for the monitoring of the Respiratory Systolic Variation Test (RSVT) can be located either in the monitor, respirator, or a separate device. The software and the monitor can accept information from the ventilator, e.g., the exact time of the start of each breath, the expired volume, the peak airway pressure, etc. After the start of each mechanical breath and during its cycle, the hemodynamic signal is tracked, and its minimal and maximal values are recorded throughout the test. The monitor is equipped to calculate and show the slopes of the minimal and maximal values of the hemodynamic parameter after the completion of the respiratory maneuver as well as the angles of the slopes of the change in maximal (upslope) and minimal (downslope) values and the ratio. It should also be possible to determine additional parameters such as the area under the curve, dp/dtmax (which is a measure of contractility), etc.

Preferably, the monitor is also equipped so as to calculate the systolic pressure variation (SPV), which is the difference between the maximal and minimal values of the hemodynamic physiological parameter, e.g., blood pressure, during one cycle of the mechanical breath. Preferably, the monitor is also able to show delta up and delta down, i.e., the degree by which the hemodynamic physiological parameter increases and decreases, respectively, in response to airway manipulation relative to its baseline during the pre-inspiratory period.

The method of the invention can be used in all mechanically ventilated patients in whom a physiological parameter that reflects left ventricular stroke volume is continuously measured. It can serve as a basic diagnostic test for the determination of volume responsiveness, which is very high during frank hypovolemia and very low or negative during congestive heart failure and/or volume overload. It may be used in anesthetized patients and in all other patients that are mechanically ventilated by any ventilatory mode. With the method of the present invention, it is hence possible to easily measure the cardiovascular status by medical equipment normally used in any mechanically ventilated patient without the need of additional complicated, costly and difficult-to-use equipment.

In the following the invention will be explained in more detail with reference to FIGS. 1–10.

Figure 1A:
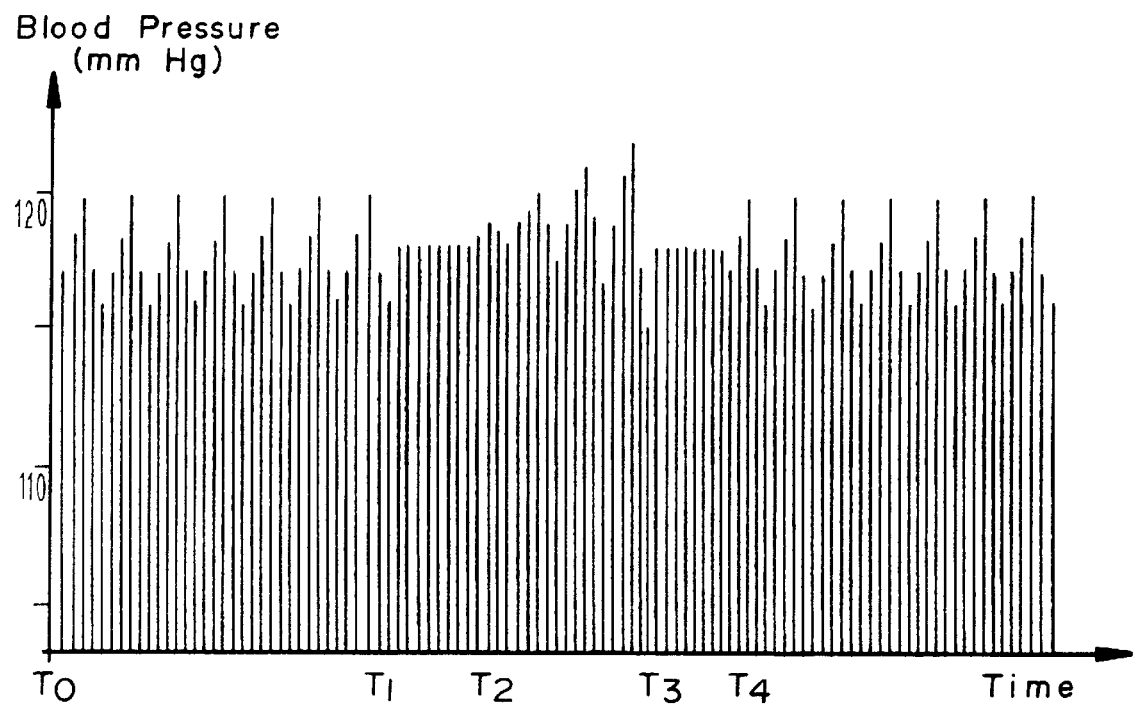
FIG. 1 is a schematic drawing of the principle of the invention.
Figure 1B:
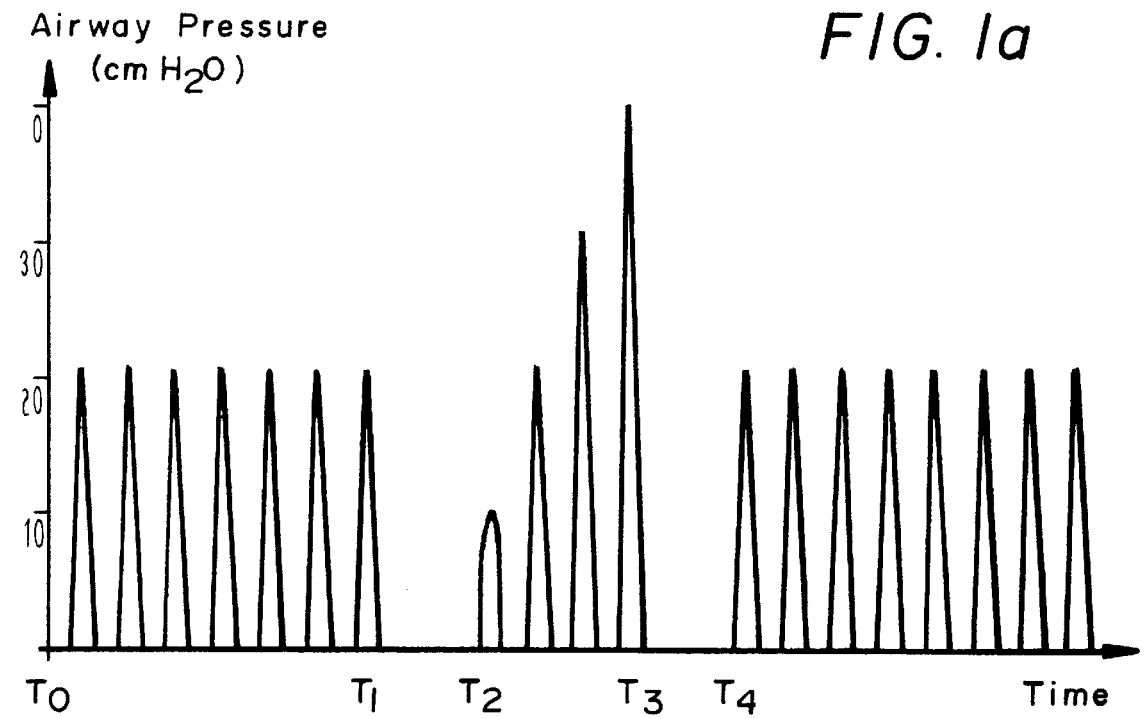

FIG. 1 is a schematic drawing explaining the principle of the present invention. In the lower part the airway pressure provided by a respirator is shown and the upper part illustrates the response of a hemodynamic variable, in which case the blood pressure is shown.

Between $T_0$ and $T_1$ normal ventilation is carried out. The response of the blood pressure is identical for each breath cycle (7 breath cycles are depicted between $T_0$ and $T_1$), showing only statistical variations. During each breath cycle the dUp and dDown in the blood pressure can be seen.

At $T_1$ short apnea is induced (optional), which ends at $T_2$. It is evident that the blood pressure is constant during the apnea, not showing any dUp or dDown.

At $T_2$ the variation of the airway pressure is initiated, starting at an airway pressure of, e.g., 10 cmH$_2$O in the first breath cycle and increasing up to, e.g., 40 cmH$_2$O in the fourth breath cycle. In the upper part of FIG. 1 the characteristic response of the blood pressure is shown. It is evident that the maximal values of the blood pressure during each breath cycle increase with increasing airway pressure and that the minimal values of the blood pressure during each breath cycle decrease with increasing airway pressure. In other words, the dependence of the dUp and dDown values on variations in airway pressure are shown.

At $T_3$ the variation of the airway pressure ends and a second short apnea (optional) is induced, leading to a constant blood pressure which can be used as a reference value for evaluating the effect of the airway pressure variation on the blood pressure.

At $T_4$ the short apnea ends and normal ventilation is continued.

Typical values for the time difference $T_0$–$T_1$ are in the region of 25 to 50 seconds i.e. about 8 to 16 breaths/min.

Typical values for the airway pressure during normal ventilation are in the region of 15 to 30 cmH$_2$O.

The maximal airway pressure which can be used during the variation of the airway pressure depends on the condition of the patient but is normally below 40 cmH$_2$O.

Figure 2:
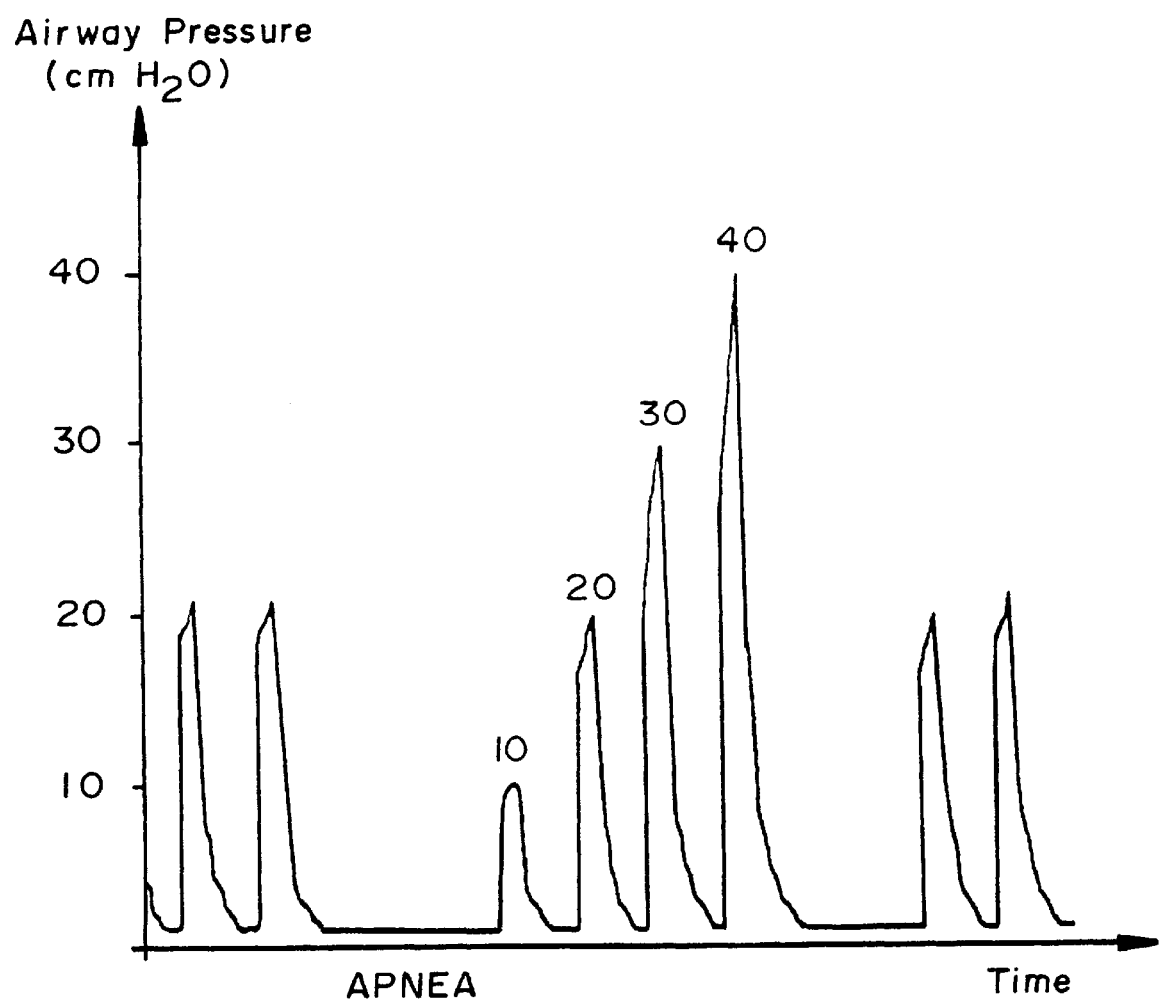
FIG. 2 is an example of a possible respiratory maneuver.

FIG. 2 shows an example of a possible respiratory maneuver consisting of four consecutive breaths. The ventilatory mode used is pressure controlled ventilation at a rate of 8/min, I:E ratio 1:3. The respiratory maneuver in this example includes five levels of pressure, namely 0, 10, 20, 30 and 40 cmH$_2$O. The specific variables, i.e., the number of breaths, and the level and duration of pressure can be changed according to the circumstances and the condition of the patient or will be fixed in the apparatus. The zero pressure level (or the PEEP level) serves for the determination of the value of the hemodynamic parameter during apnea.

Figure 3A:
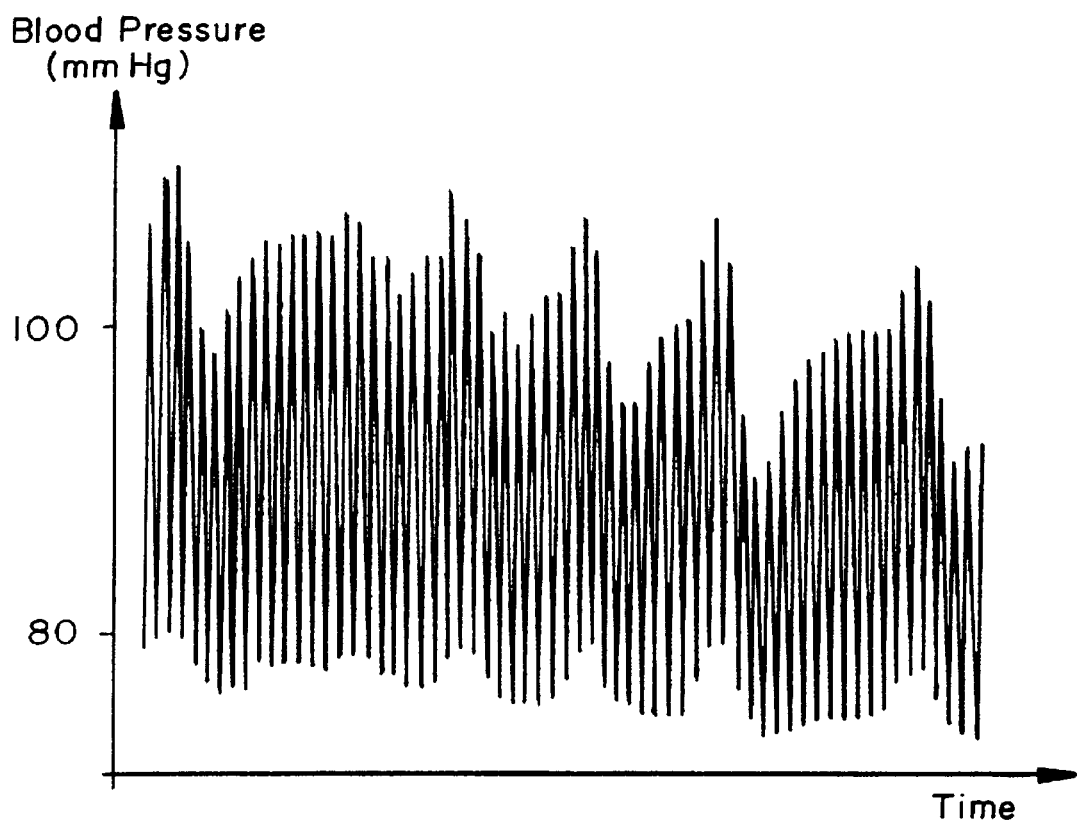
FIGS. 3a to 3d show the steps of the analysis of the changes in the systolic pressure during the RSVT.
Figure 3B:
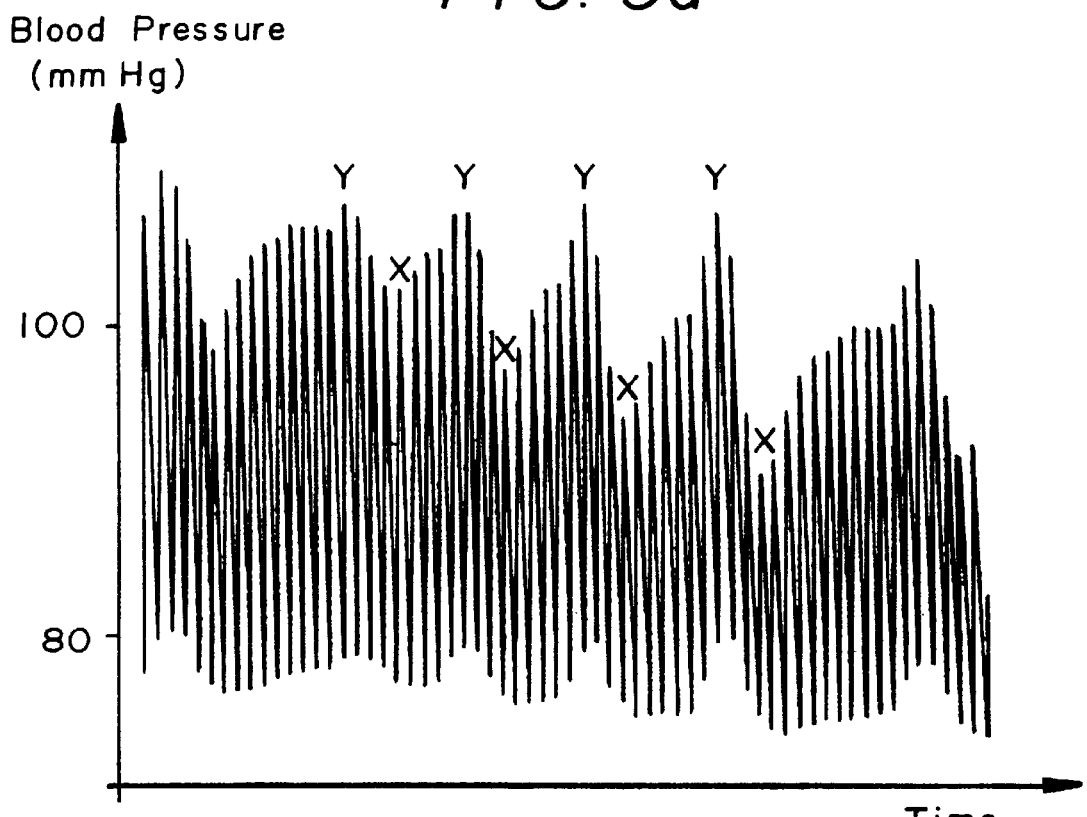

FIG. 3a shows the response of a hemodynamic parameter (in this case the blood pressure) to a respiratory maneuver as shown in FIG. 2. FIG. 3b exemplifies the identification of the minimal (X) and maximal (Y) systolic values after each change in airway pressure, i.e. during each of the four cycles of mechanical breaths.

Figure 3C:
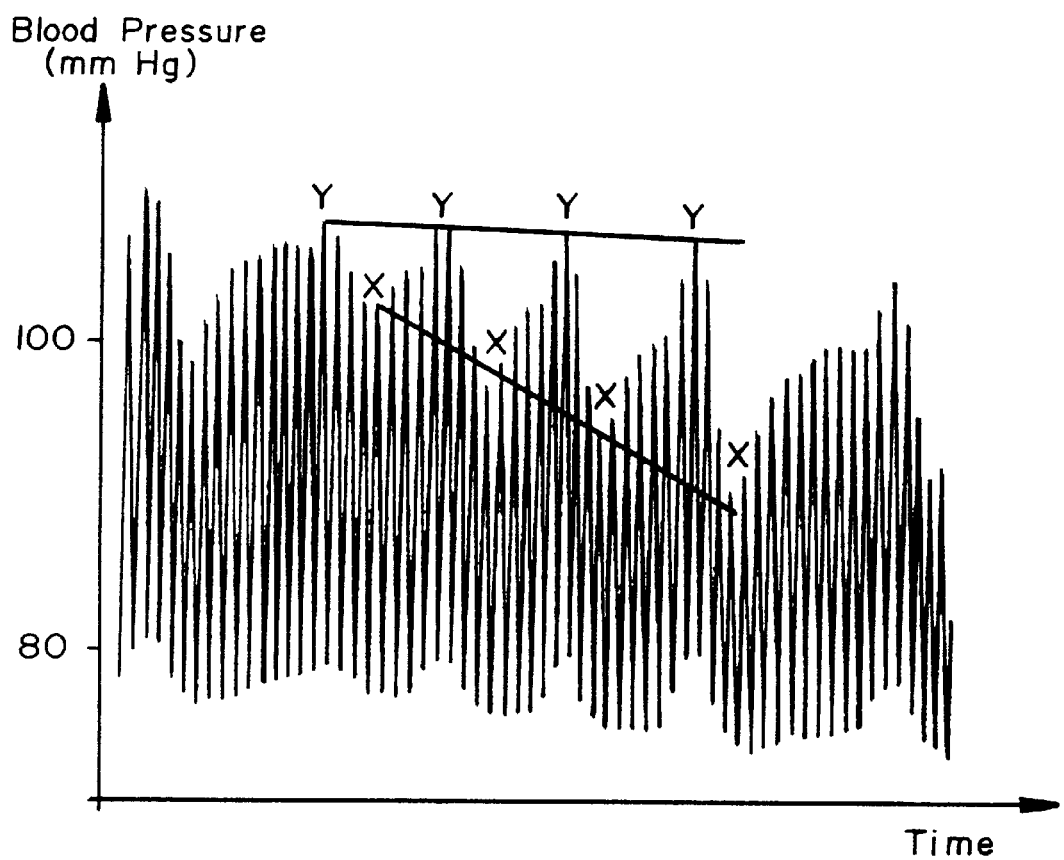

FIG. 3c shows the lines of best fit for the minimal (X) and maximal (Y) values.

Figure 3D:
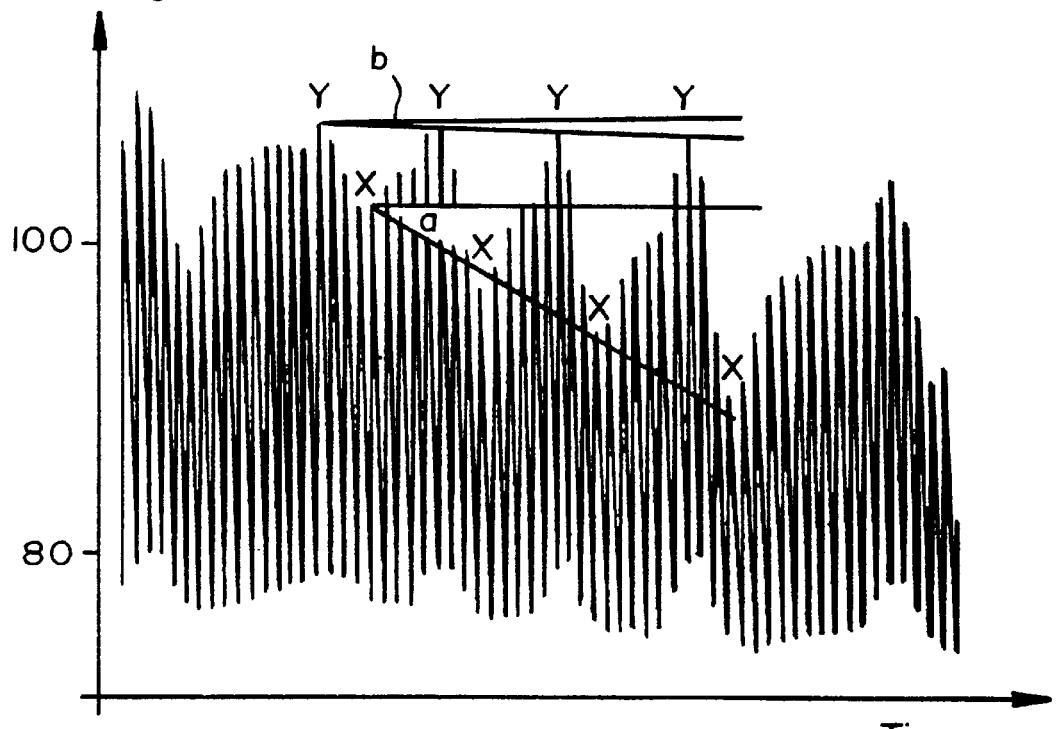

FIG. 3d exemplifies the calculation of the slope of each line characterized by angle a for the downslope and angle b for the upslope. Downslope X is a measure of volume responsiveness while upslope Y is a measure of cardiac (stroke) output augmentation.

Figure 4B:
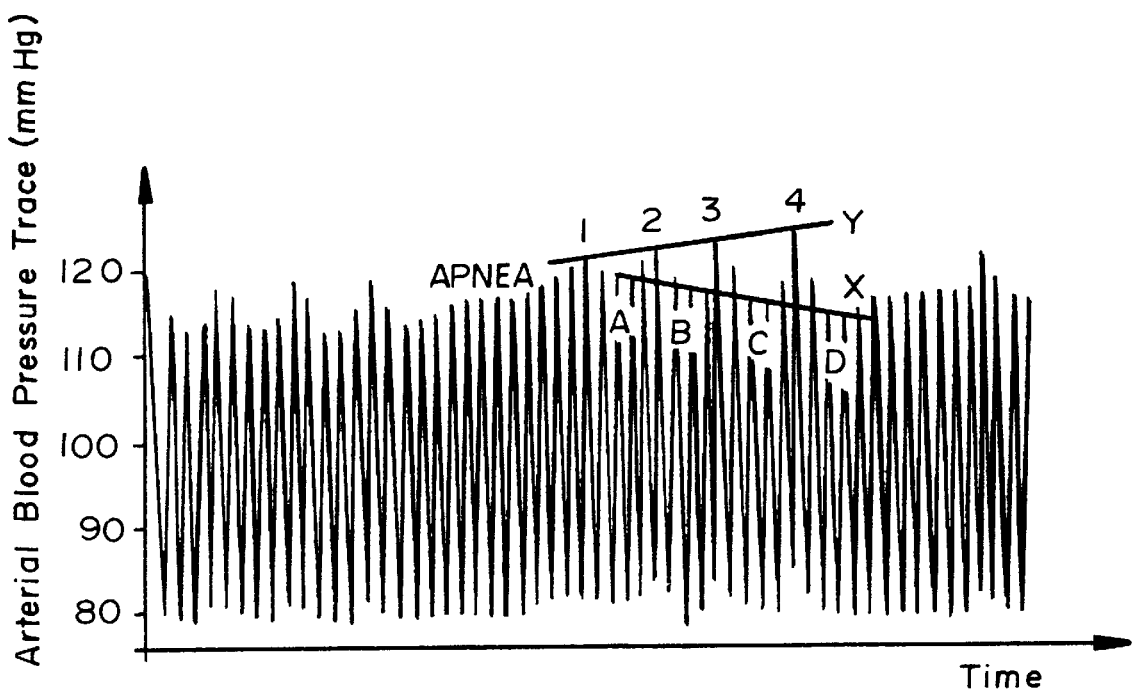
FIG. 4 is the trace of airway pressure during the respiratory maneuver (FIG. 4a) accompanied by a trace of the arterial blood pressure in a volume responsive state (FIG. 4b).
Figure 4A:
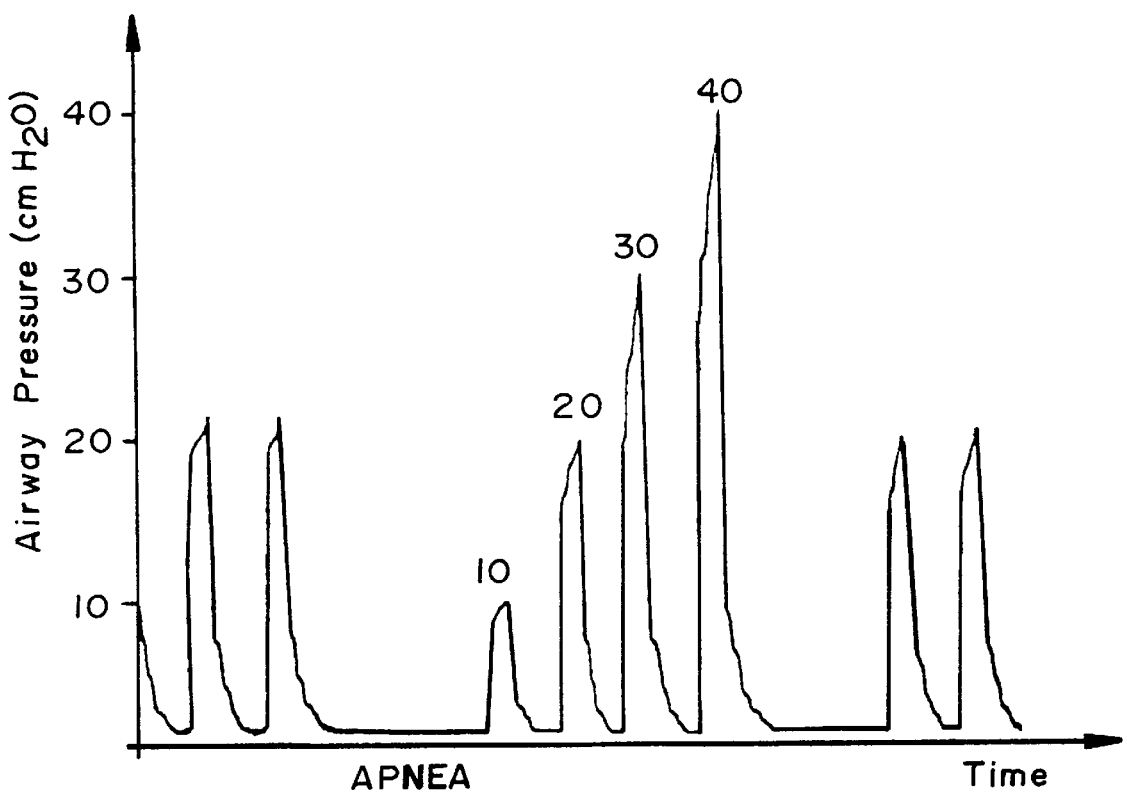

In FIG. 4 a respiratory maneuver and the resulting changes in the arterial blood pressure which occur in a volume responsive normal patient are shown. The gradual significant decreases in the systolic pressure after each breath (accounting for the steep line of best fit) are significant for the volume responsiveness of the patient.

Figure 5:
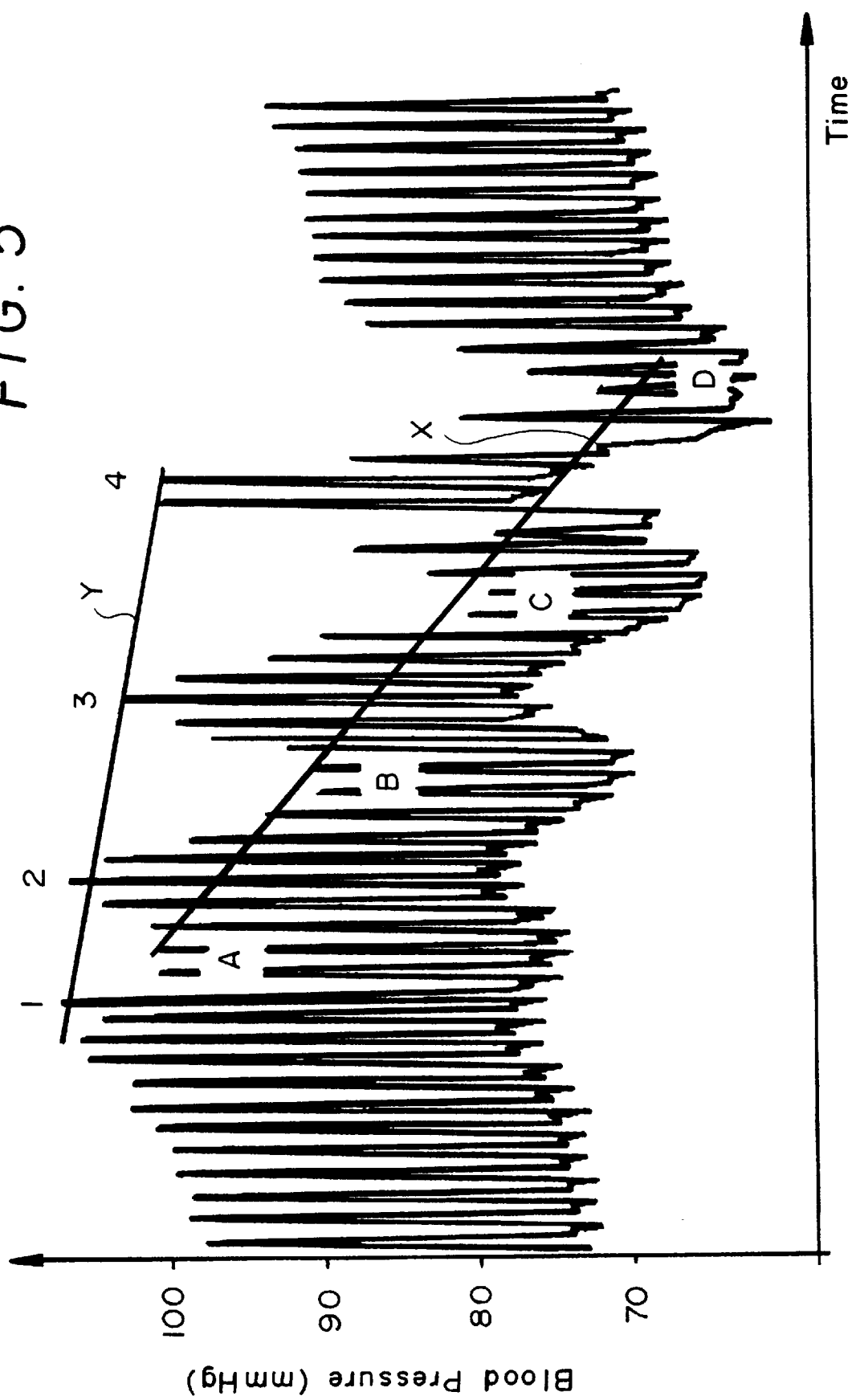
FIG. 5 shows the respiratory systolic variation test (RSVT) of the present invention in a hypovolemic patient.

FIG. 5 shows how a hemodynamic variable (in this case also the blood pressure) responds to the respiratory maneuver of the present invention if the patient is very hypovolemic. The diagnosis of hypovolemia can be made by a skilled person by looking at the steepness of line X connecting the minimal systolic values (A,B,C,D). Even the slope of line Y, connecting the maximal values (1,2,3,4), is slightly negative, thus confirming the diagnosis of severe hypovolemia.

Figure 6A:
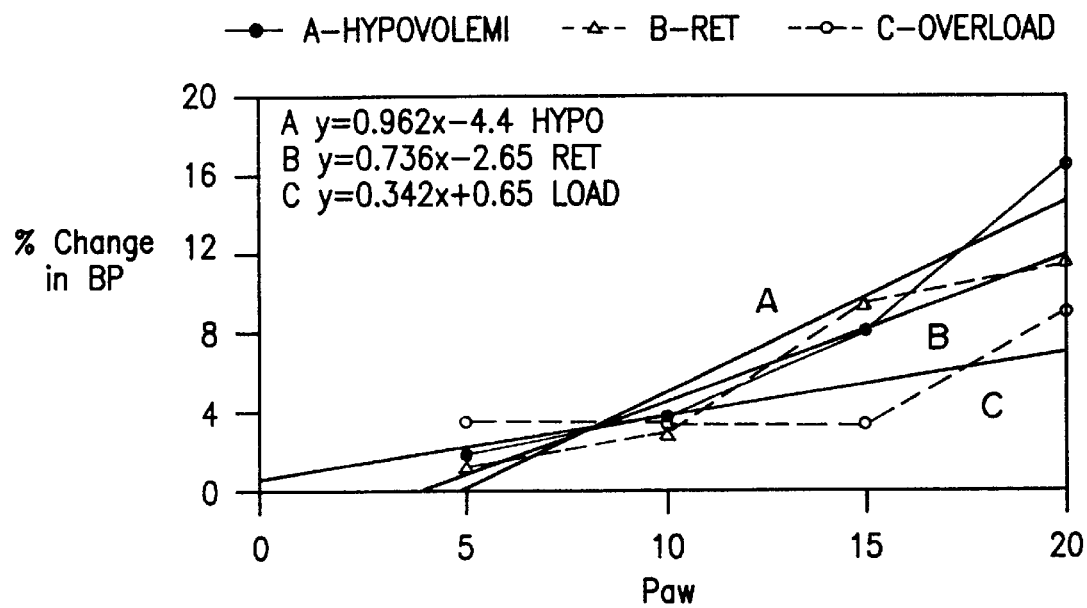
FIG. 6 shows the angles of the RSVT in dog #1 (FIG. 6a) and dog #2 (FIG. 6b) subjected to bleeding, retransfusion and volume overload.
Figure 6B:
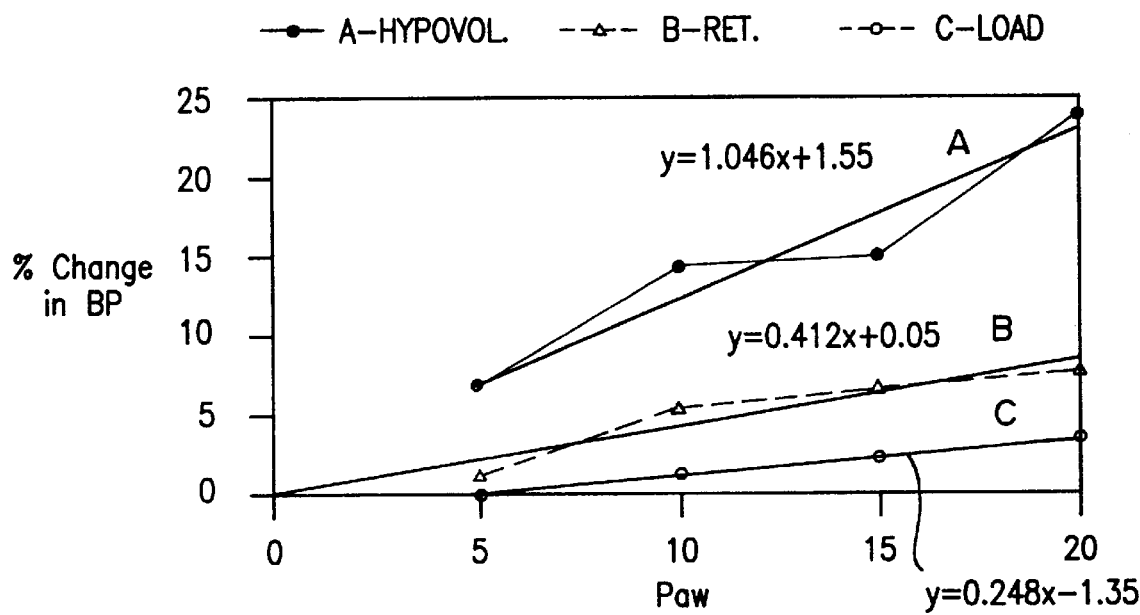

FIG. 6 depicts an example of a possible analysis of the changes in the blood pressure curve following the respiratory maneuver of the present invention in two dogs during bleeding of 30% of estimated blood volume (A), retransfusion of shed blood (B), and additional volume overload (C). In this figure the Y axis is the t of change in the blood pressure at four levels of airway pressure (X axis). It can be clearly seen that depending on the volume states, slope a in equation y=ax+b varies, the slope during hypovolemia being the steepest while the slope during volume overload being the flattest. Therefore, the slope of the hemodynamic variable during the respiratory maneuver allows a skilled person to decide whether fluid transfusion should be made in a patient having symptoms of impending circulatory failure, or whether a volume overload has already occurred, so that other therapeutic measures are necessary.

Figure 7A:
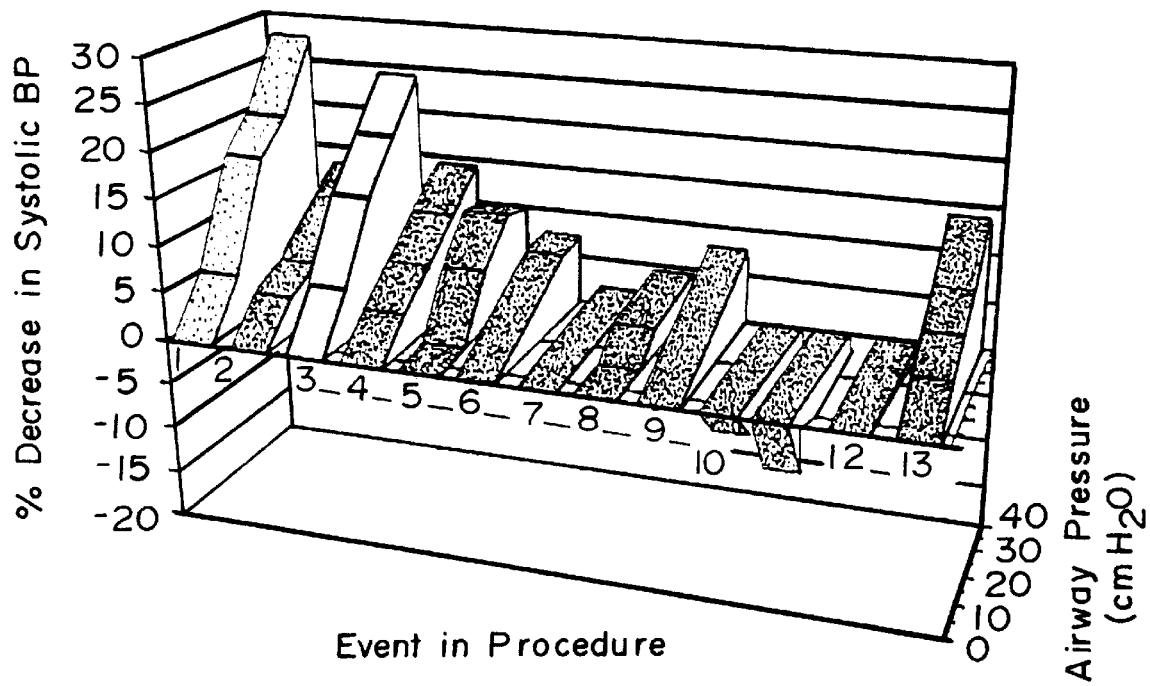
FIGS. 7a and 7b show the graphic display of the changes in the downslope and upslope of the RSVT during a case of aortic surgery.
Figure 7B:
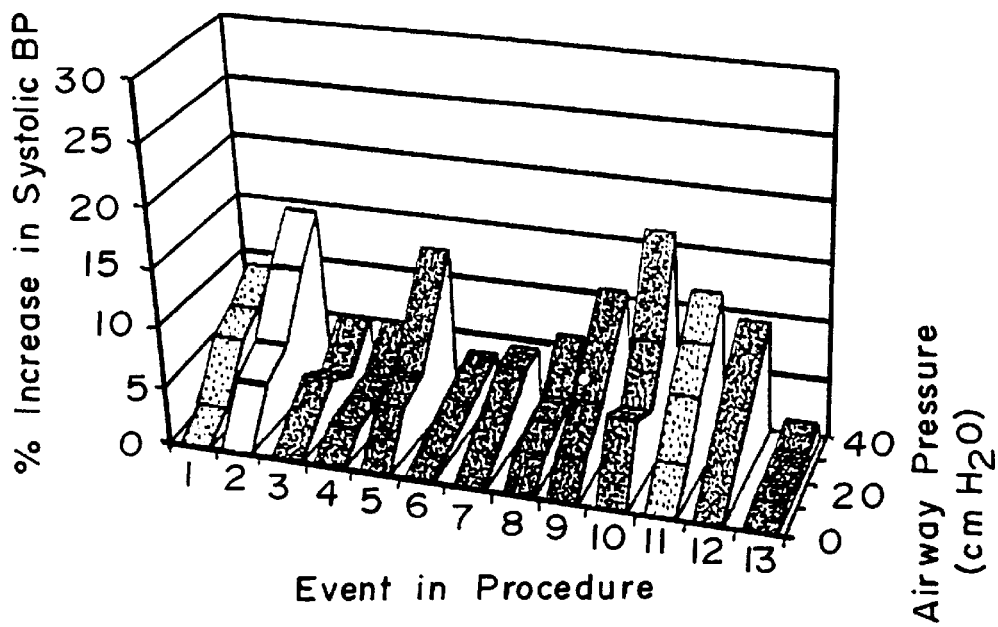

In FIGS. 7a and 7b the repetitive use of the method of the present invention during aortic surgery is demonstrated, Points 1–13 denote the following intraoperative events:

1. Significant hypovolemia due to bleeding (prior to clamping);
2. immediately after aortic clamping;

3. several minutes after clamping during drop in blood pressure;
4. after infusion of one liter and during light anesthesia;
5. after addition of nitrous oxide;
6. additional volume replacement with blood and hemaecel;
7. following epidural injection of 25 mg bupivacaine (Marcaine);
8. prior to unclamping;
9. dopamine infusion started prior to unclamping;
10. immediately after unclamping first leg;
11. immediately after unclamping second leg;
12. after bolus dopamine due to hypotension unresponsive to volume replacement; and
13. after addition of nitroglycerin (0.8 mg/kg/min) and 25 mg epidural bupivacaine (Marcaine) for hypertension.

FIG. 7a depicts the change in the downslope of the four minimal systolic values during the procedure. The exaggerated volume responsiveness at points 1–4 and 13 can be clearly seen while points 7, 8, 10, 11 and 12 are characterized by a lack of change in the systolic blood pressure during the respiratory maneuver of the present invention, thereby denoting a non-volume responsive state and indicating to a skilled person that a blood transfusion would probably not be of too much use, while cardiotonic agents may improve cardiac function, if so desired.

FIG. 7b depicts the change in the upslope, i.e., the maximal systolic values during the RSVT, during the procedure. Points 10–12 are characterized by steep upslopes and flat downslopes from which a skilled person can take that the filling pressures are high and that possibly a significant reduction in cardiac contractility (heart failure) has occurred.

Figure 8:
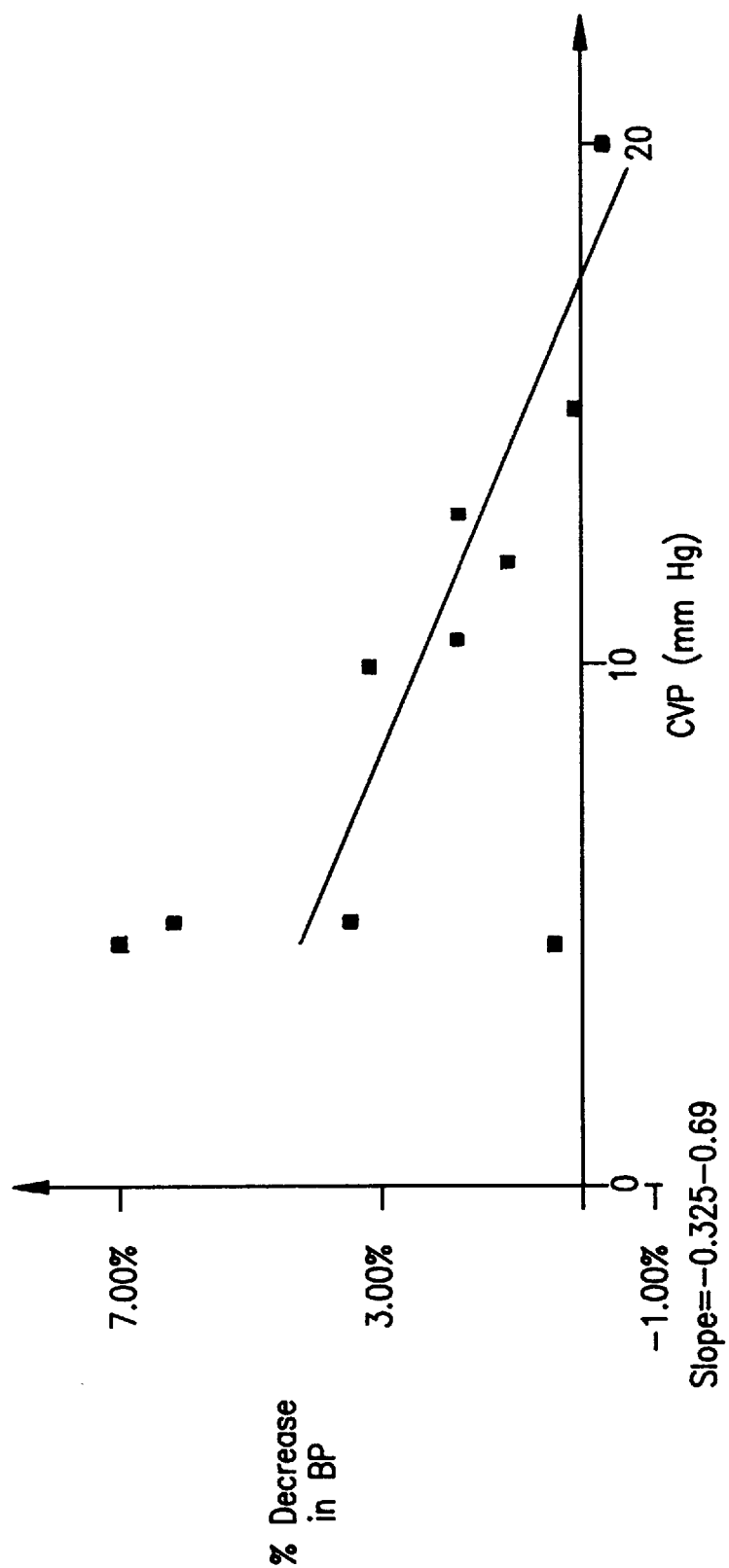
FIG. 8 shows the relation of the downslope of the RSVT and the CVP values during this procedure of aortic surgery.
Figure 9A:
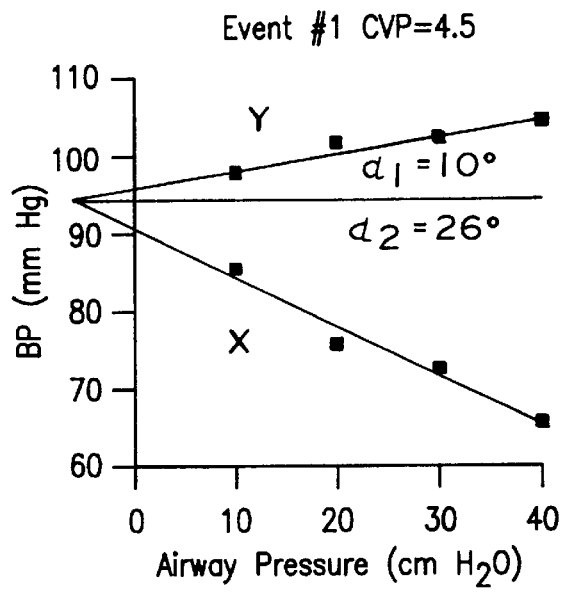
FIG. 9 shows the change in the ratio of the angles of the upslope (Y) and downslope (X) at different CVP values.
Figure 9B:
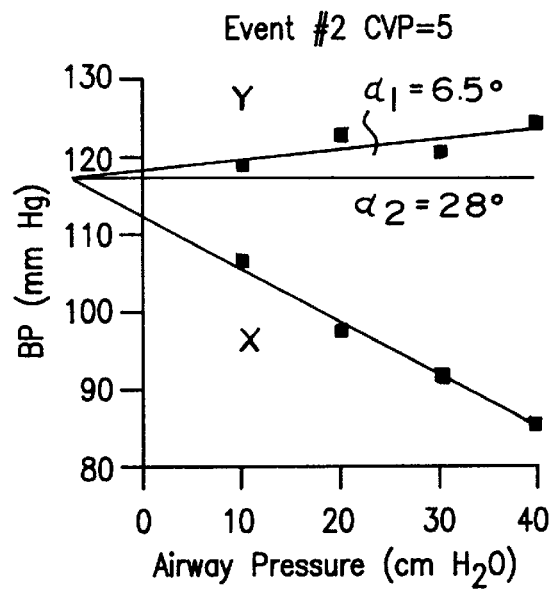
Figure 9C:
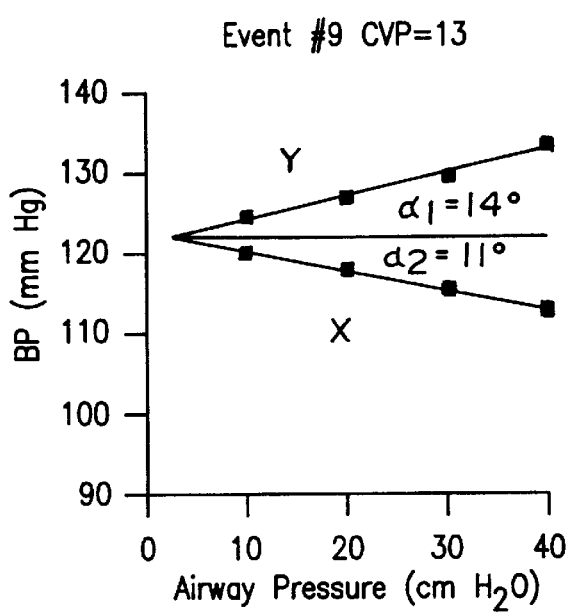
Figure 9D:
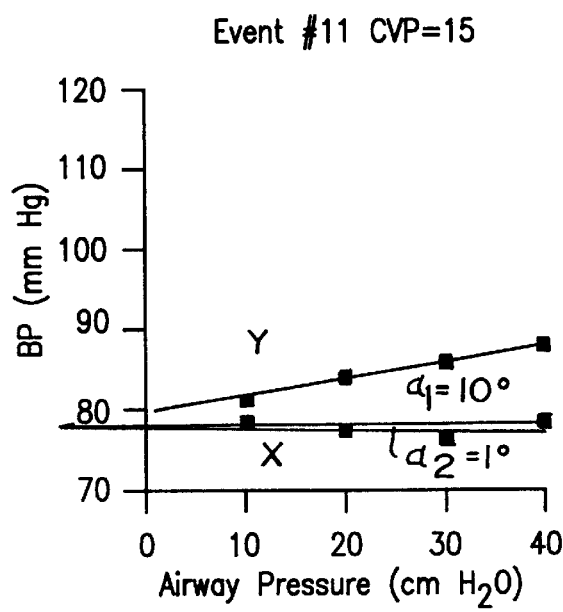

In FIG. 8 the relation between the t change in the minimal systolic values during the method of the present invention and the CVP (a method of the prior art discussed above) during this case of aortic surgery is shown. The r value is −0.69 and actually closer to −1 if the outlier is disregarded. This shows a significant correlation between the CVP measured by the complicated methods of the prior art and the minimal systolic values easily measured according to the present invention.

In FIG. 9 events 1, 2, 9 and 11 of aortic surgery as explained in FIG. 7 were used to show that the ratio between the angles of the downslope (X) and upslope (Y) change at different values of the central venous pressure (CVP). Low CVP values are associated with greater $\alpha_2$ angles, which reflect hypovolemia, thereby giving a skilled person helpful means in establishing this diagnosis. It should be noted that the X-slope expressed by $\alpha_2$ decreases and that the Y-slope ($\alpha_1$) increases at higher CVP values.

Figure 10:
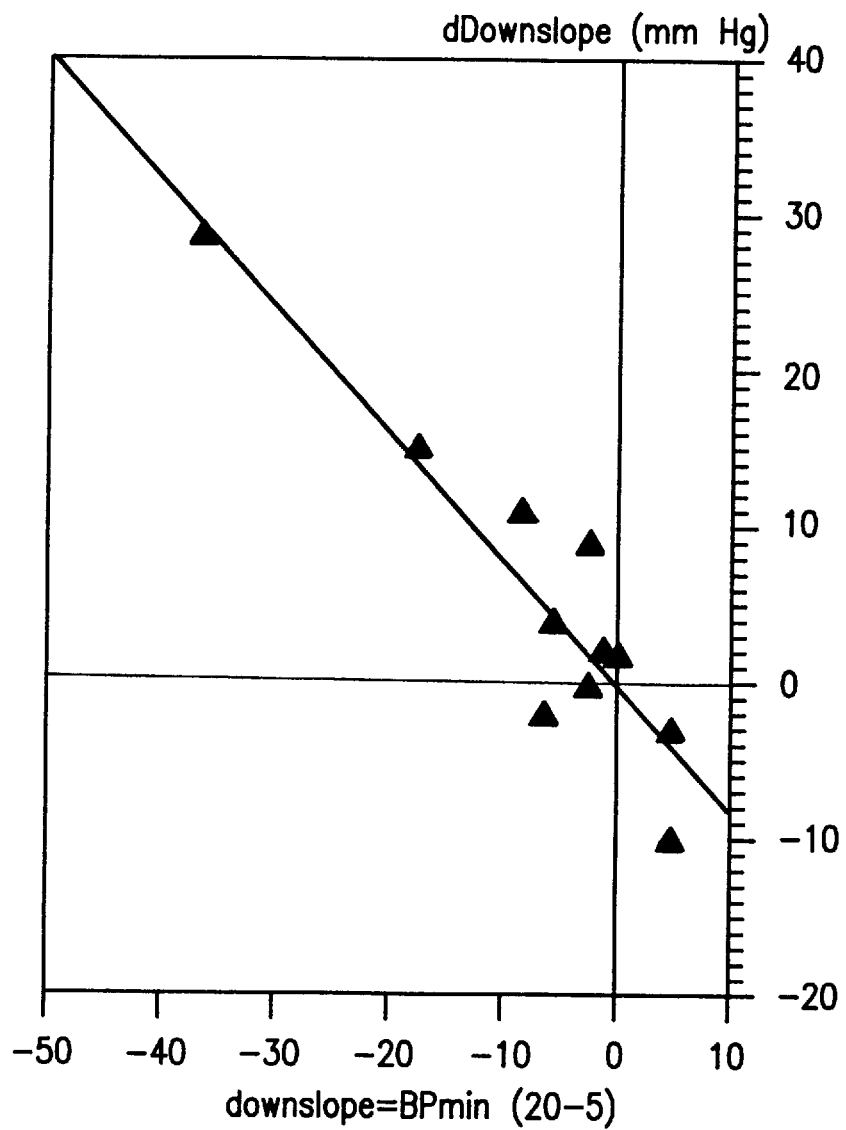
FIG. 10 shows the response of the downslope to volume loading in 11 patients.

FIG. 10 shows the results of volume loading in 11 patients. In this graph the downslope on the X axis is the difference between the minimal systolic blood pressure after two breaths of 20 and 5 ml/kg, i.e. downslope=SBPmin20−SBPmin5. The dDownslope, on the Y axis is the change in the downslope after volume loading in 11 patients. The graph shows that higher baseline downslopes are associated with a more significant response to volume loading. Thus the method of the present invention can also be used to follow the effects of volume administration,

I claim:

1. A method for cardiovascular assessment in patients ventilated with at least one of a predetermined tidal volume and pressure, which comprises:
   (a) varying said at least one of the tidal volumes and pressure levels in at least one breath cycle,
   (b) measuring a hemodynamic parameter in response to each variation according to step (a); and
   (c) assessing a cardiovascular status of a patient based on a degree of change of the hemodynamic parameter in response to the variation in said at least one of the tidal volumes and pressure levels.

2. The method according to claim 1 wherein step (a) is applied after inducing a short apnea period.

3. The method according to claim 1 or 2 wherein the hemodynamic parameter in step (b) is selected from the group of the blood pressure, the plethysmographic signal, the Doppler and echo signals.

4. The method according to claim 1 or 2 wherein, in said measuring step, the measuring of the hemodynamic parameter is performed continuously.

5. The method according to claim 1 or 2, wherein said measuring step comprises measuring peak and trough values of the hemodynamic parameter.

6. The method according to any one of claims 1 or 2, comprising the step of analyzing the measured hemodynamic parameter.

7. The method according to claim 6 wherein said analyzing step comprises at least one of the following analytic calculating steps:
   (i) calculating an area under a curve of the hemodynamic parameter in a certain region,
   (ii) calculating a difference between peak and trough values and a reference value measured during a short induced apnea, and
   (iii) calculating a slope of a line of best fit of peak and trough values, respectively.

8. The method according to claim 1 or 2, wherein the hemodynamic parameter is a left ventricular output related parameter.

9. The method according to claim 1, wherein said measuring step is initiated upon external demand.

10. The method according to claim 1, wherein a plurality of breath cycles with varying magnitude said at least one of the tidal volumes and pressure levels are used.

11. The method according to claim 1, wherein said measuring step is initiated automatically in preset time intervals.

12. The method according to claim 1, wherein from 2 to 10 breath cycles with varying magnitude of said at least one of the tidal volumes and pressure levels are used.

13. The method according to claim 1, wherein from 2 to 4 breath cycles with varying magnitude of said at least one of the tidal volumes and pressure levels are used.

* * * * *